(12) United States Patent
Stad et al.

(10) Patent No.: US 7,806,901 B2
(45) Date of Patent: Oct. 5, 2010

(54) ARTHROPLASTY FINAL SEATING INSTRUMENTS

(75) Inventors: Shawn Stad, Fall River, MA (US); Mark Gracia, Rochester, MA (US)

(73) Assignee: Depuy Spine, Inc., Raynham, MA (US)

( * ) Notice: Subject to any disclaimer, the term of this patent is extended or adjusted under 35 U.S.C. 154(b) by 510 days.

(21) Appl. No.: 11/378,813

(22) Filed: Mar. 17, 2006

(65) Prior Publication Data

US 2007/0233152 A1    Oct. 4, 2007

(51) Int. Cl.
  *A61B 17/58* (2006.01)
  *A61B 17/60* (2006.01)
  *A61F 2/00* (2006.01)
(52) U.S. Cl. .................... 606/99; 623/17.14
(58) Field of Classification Search .............. 606/61, 606/99, 279, 246; 623/17.11–17.16
See application file for complete search history.

(56) References Cited

U.S. PATENT DOCUMENTS

| 4,898,161 | A | 2/1990 | Grundei |
| 5,556,431 | A | 9/1996 | Buttner-Janz |
| 5,674,296 | A | 10/1997 | Bryan |
| 6,261,296 | B1 | 7/2001 | Aebi et al. |
| 6,277,122 | B1 | 8/2001 | McGahan et al. |
| 6,440,142 | B1 | 8/2002 | Ralph et al. |
| 6,582,437 | B2 | 6/2003 | Dorchak et al. |
| 6,589,247 | B2 | 7/2003 | McGahan et al. |
| 6,648,888 | B1 | 11/2003 | Shluzas |
| 6,712,825 | B2 | 3/2004 | Aebi et al. |
| 6,716,218 | B2 | 4/2004 | Holmes et al. |
| 6,719,760 | B2 | 4/2004 | Dorchak et al. |
| 7,063,725 | B2 | 6/2006 | Foley |
| 7,081,118 | B2 | 7/2006 | Weber et al. |
| 7,115,132 | B2 | 10/2006 | Errico et al. |
| 7,169,182 | B2 | 1/2007 | Errico et al. |
| 7,316,686 | B2 | 1/2008 | Dorchak et al. |
| 7,575,576 | B2 | 8/2009 | Zubok et al. |
| 7,632,281 | B2 | 12/2009 | Errico et al. |
| 2001/0029377 | A1 | 10/2001 | Aebi et al. |
| 2003/0225416 | A1 | 12/2003 | Bonvallet et al. |
| 2004/0106927 | A1 | 6/2004 | Ruffner et al. |
| 2004/0167536 | A1 | 8/2004 | Errico et al. |
| 2004/0220582 | A1* | 11/2004 | Keller ................. 606/99 |
| 2006/0030860 | A1* | 2/2006 | Peterman ............ 606/99 |

FOREIGN PATENT DOCUMENTS

WO    WO 2004/064692 A2 *    5/2004

OTHER PUBLICATIONS

Capasso, "Mechanical behaviour of two types of vertebral distractors submitted to compressions-flexion tests", Ital J Orthop Traumatol, 1987 Mar., pp. 121-126, vol. 13(1). (abstract only).
Rutskii, "Designing a dynamic spinal distractor", Med Tekh., 1995 Jul.-Aug., pp. 29-32, vol. 4 (abstract only).
Demetropoulos, "Development and calibration of a load sensing cervical distractor capable of withstanding autoclave sterilization", Med Eng Phys., 2005 May, pp. 343-346, vol. 27(4). Epub Dec 8, 2004.

* cited by examiner

*Primary Examiner*—Thomas C Barrett
*Assistant Examiner*—Andrew Yang

(57) ABSTRACT

An instrument for finally seating an endplate of an intervetebral motion disc.

2 Claims, 10 Drawing Sheets

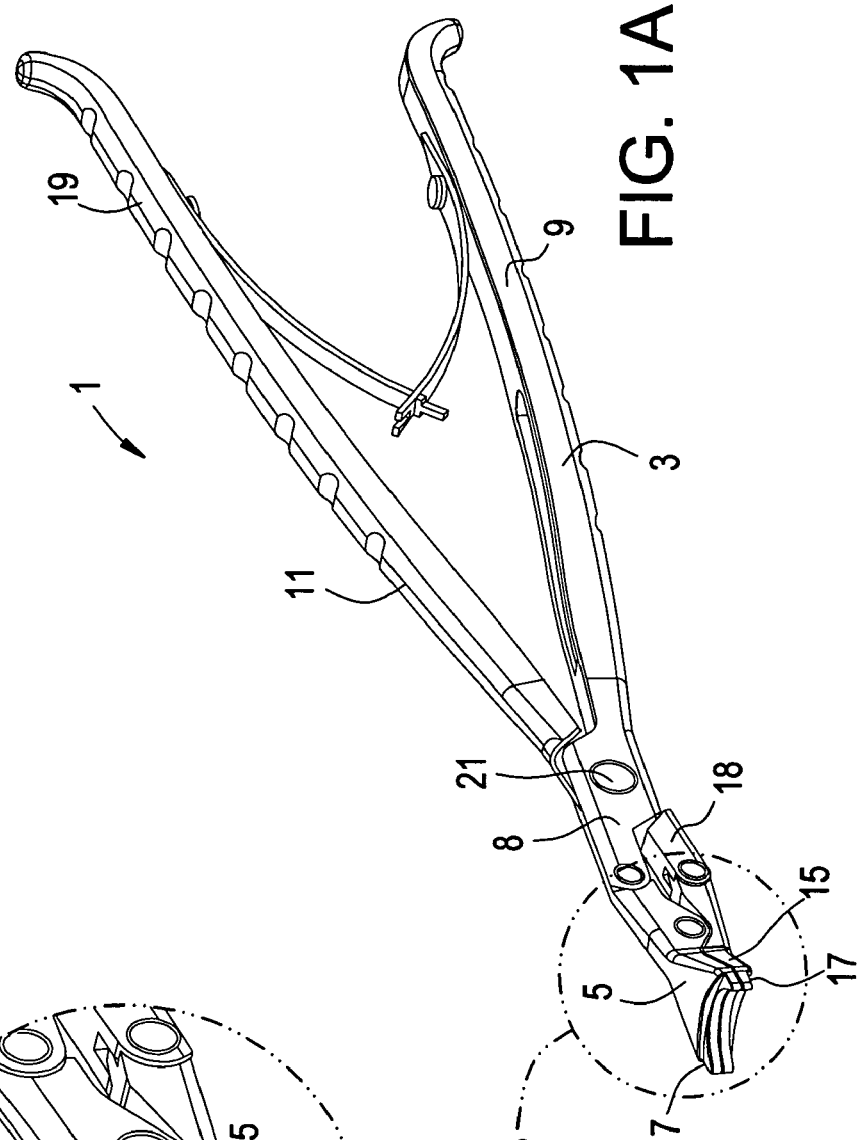
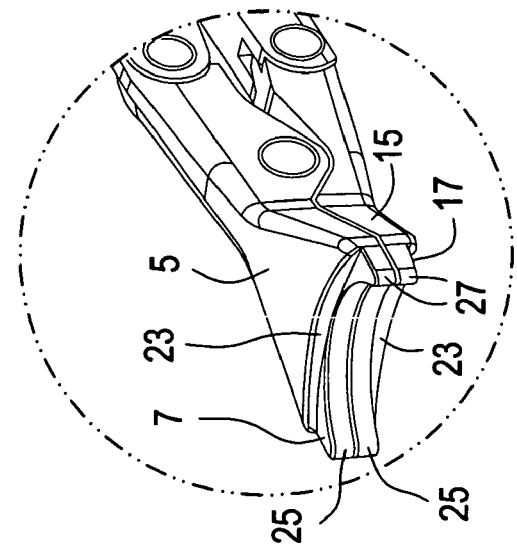

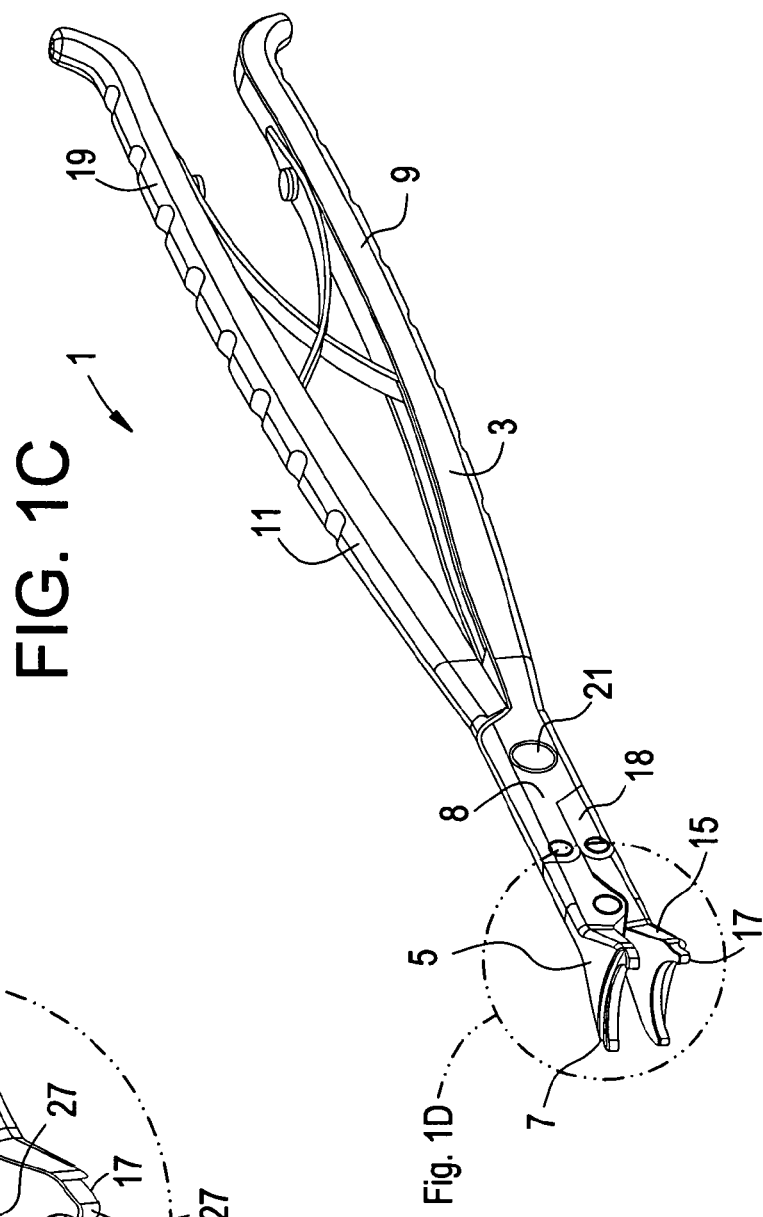

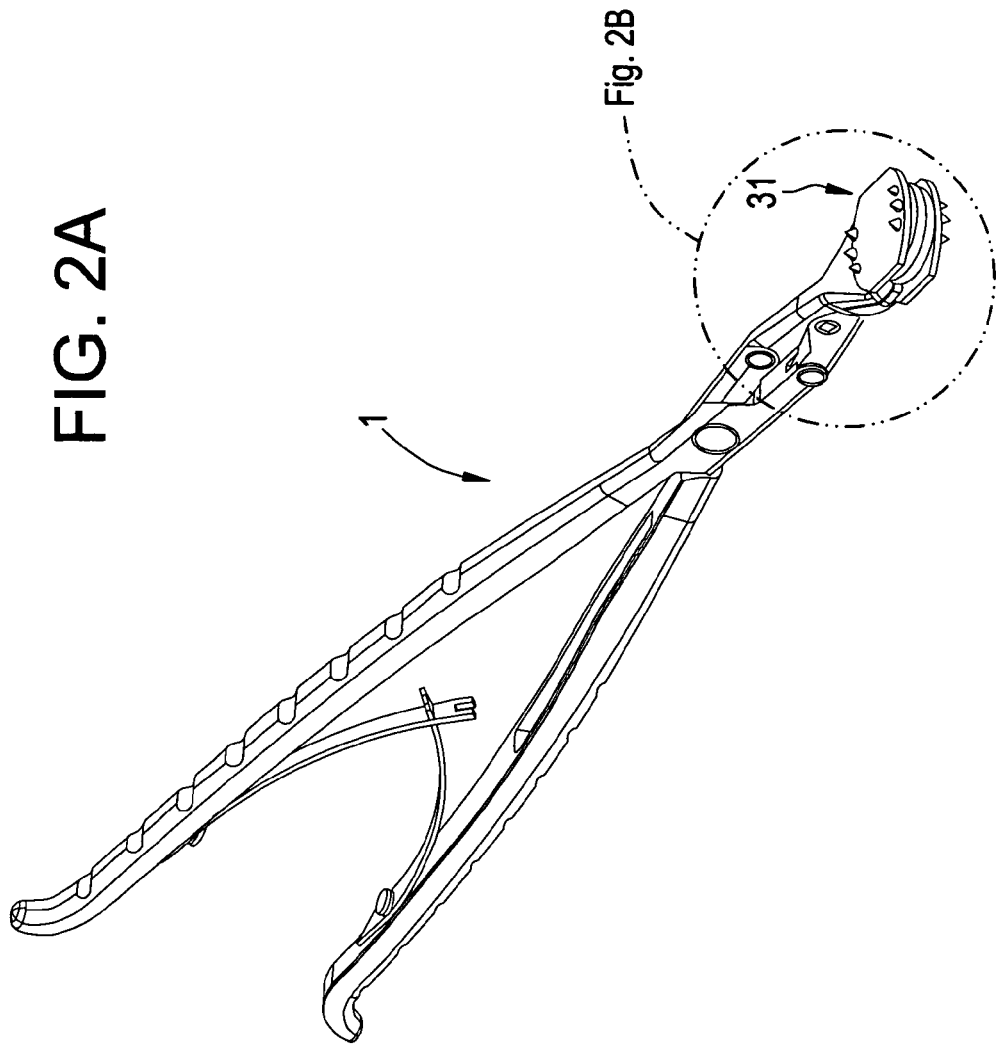
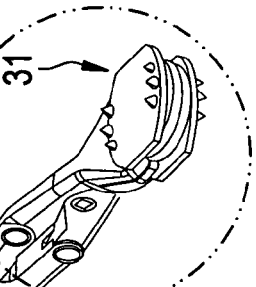
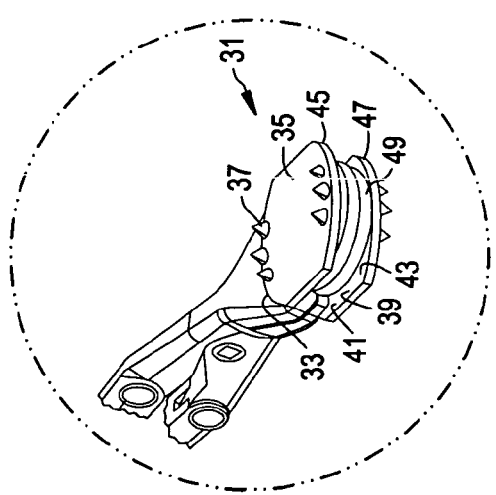

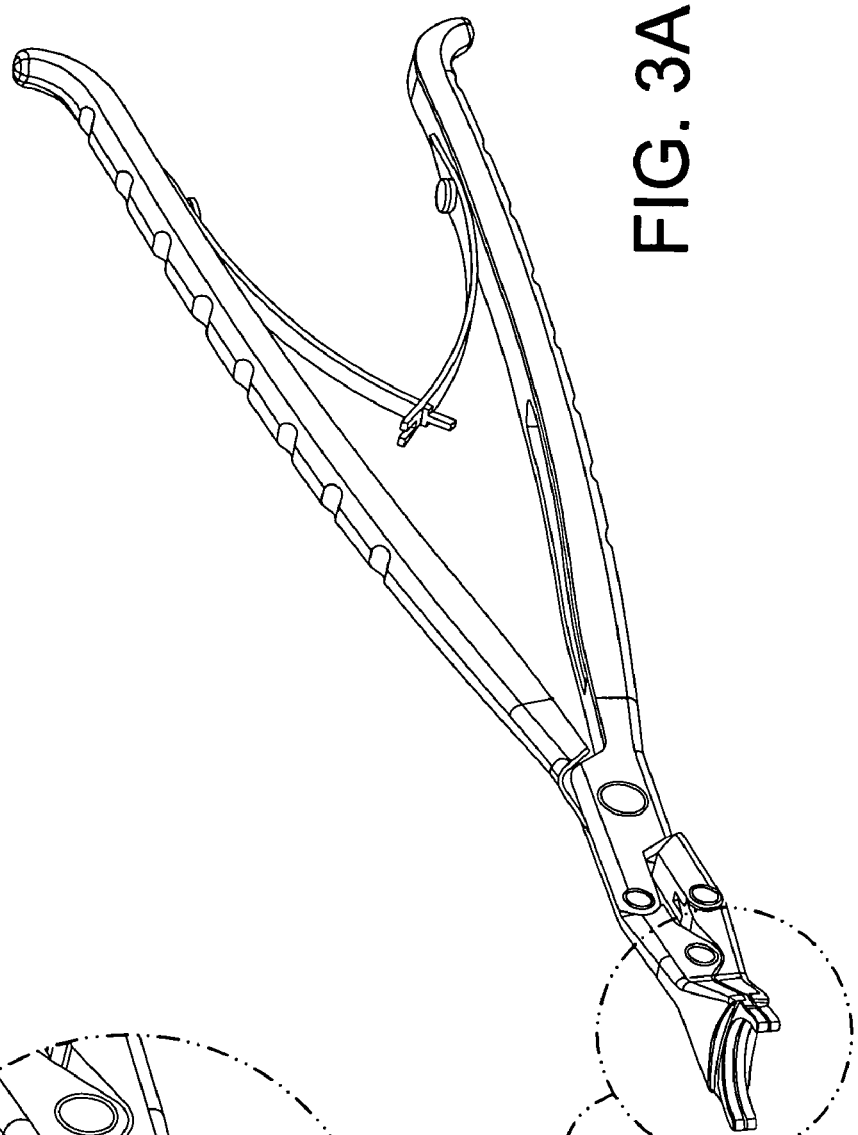
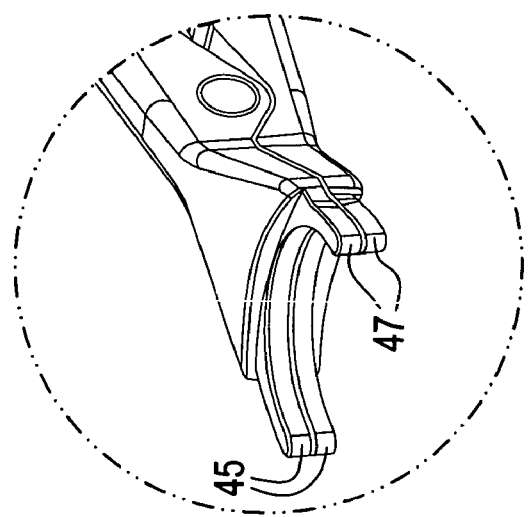

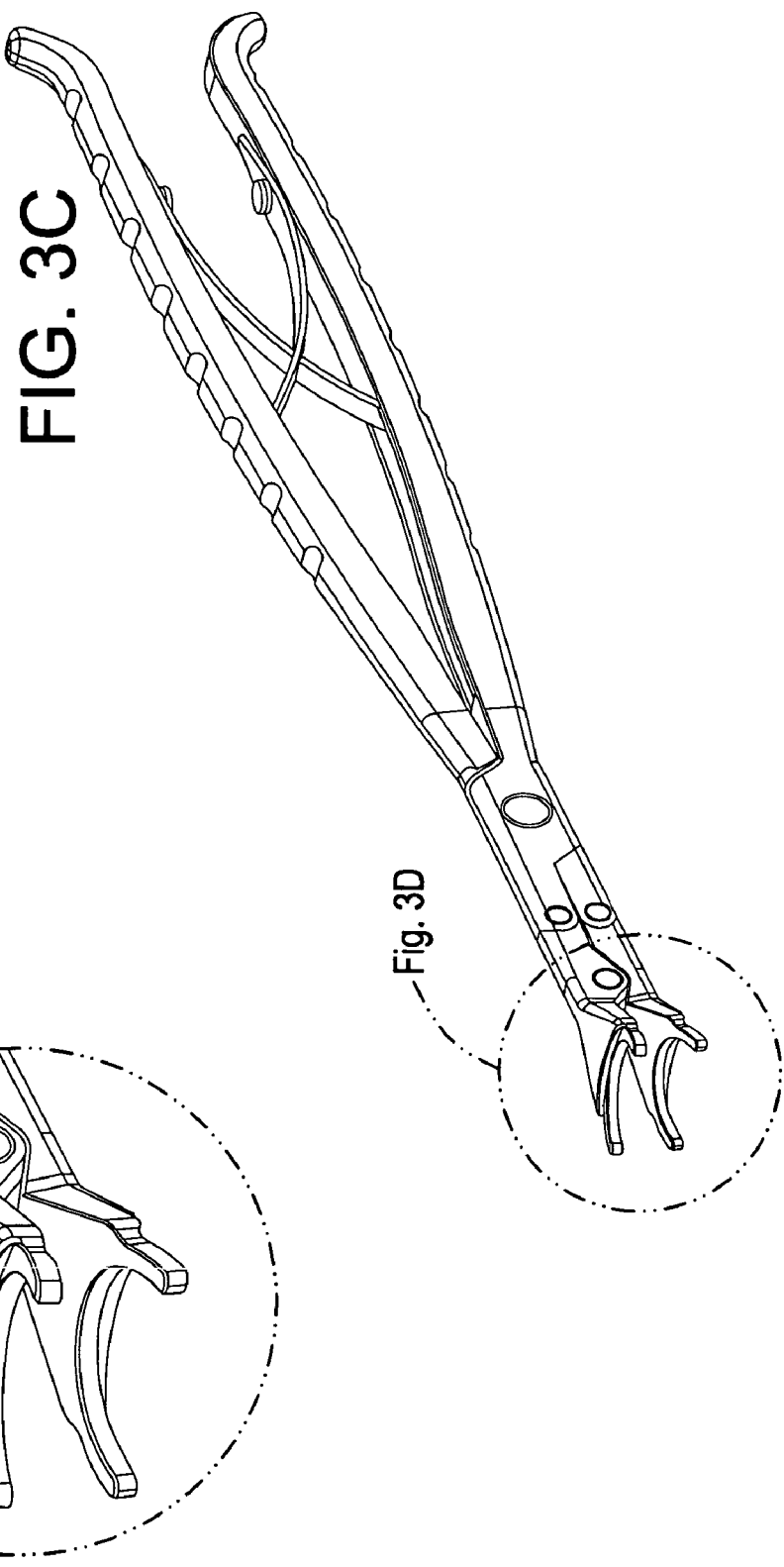

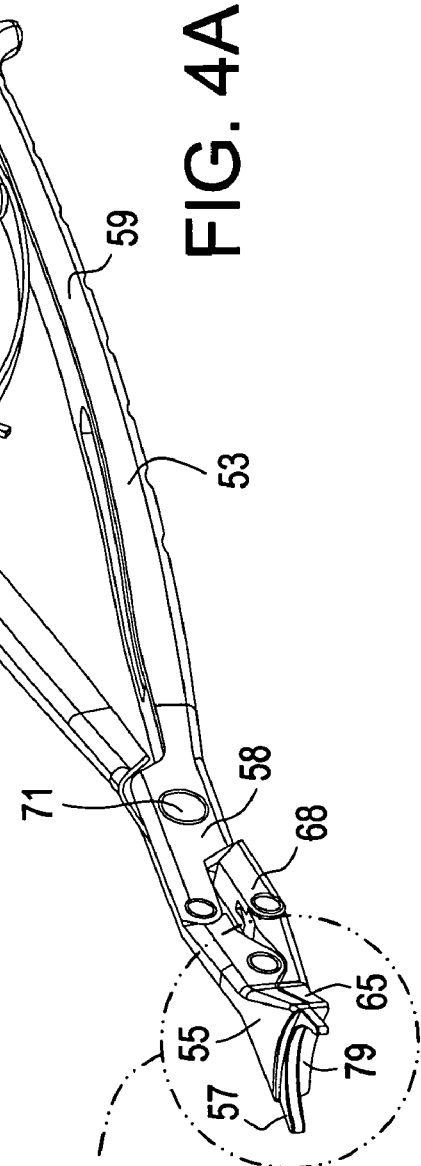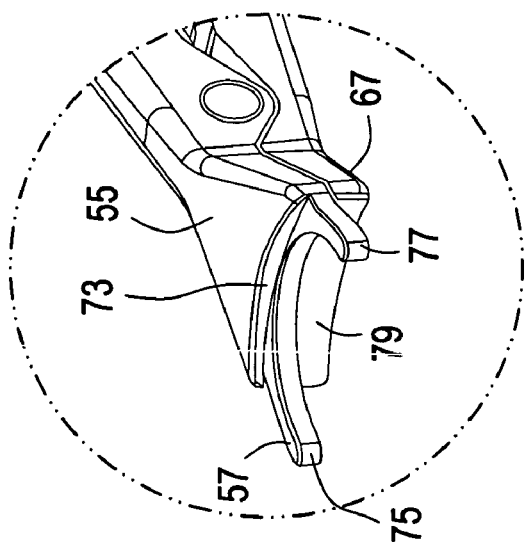

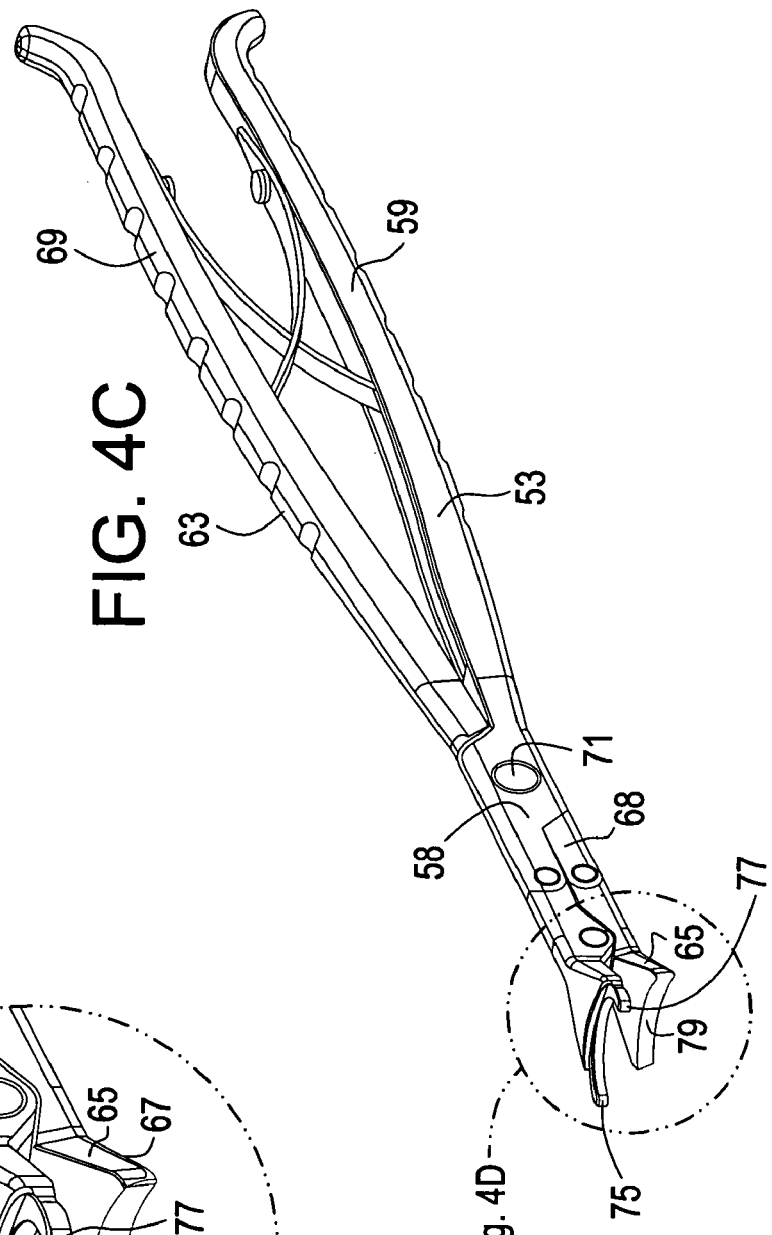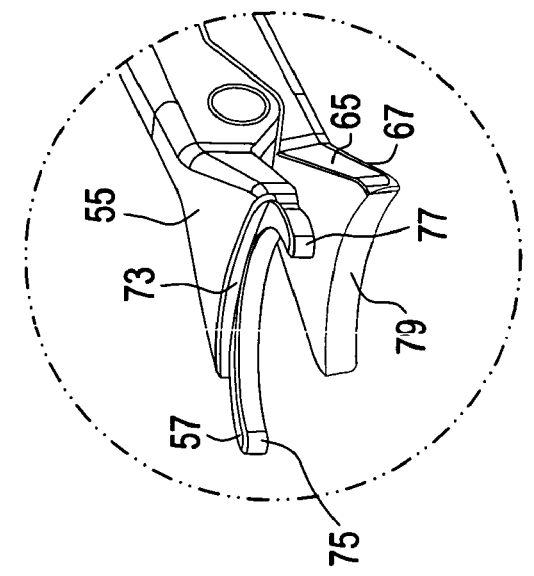

ns7
ARTHROPLASTY FINAL SEATING INSTRUMENTS

BACKGROUND OF THE INVENTION

The leading cause of lower back pain arises from rupture or degeneration of lumbar intervertebral discs. Pain in the lower extremities is caused by the compression of spinal nerve roots by a bulging disc, while lower back pain is caused by collapse of the disc and by the adverse effects of articulation weight through a damaged, unstable vertebral joint. One proposed method of managing these problems is to remove the problematic disc and replace it with a prosthetic disc that allows for the natural motion between the adjacent vertebrae ("a motion disc").

As arthroplasty becomes a more common method of treating degenerative disc disease and low back pain, there will be a greater need to ensure that the implant is properly seated to avoid the occurrence of implant migration. However, as spine arthroplasty is relatively new to the global spine community, there is a lack of instrumentation available to assist the surgeons with intraoperative adjustments to the implant positioning.

Therefore, it is an objective of the present invention to provide an instrument that assists with the intraoperative or final positioning of a spine arthroplasty device to reduce the potential for implant migration.

SUMMARY OF THE INVENTION

The present invention relates to an instrument that can be used for the final seating of an intervertebral motion disc implant that has already been inserted into the disc space by pressing its fixation teeth, keels or other fixation fixtures present upon the outer surface of the prosthetic endplates into the bony endplates of the patient, thereby reducing the potential for implant migration.

This instrument is adapted to be inserted between opposing prosthetic endplates that have been inserted into the disc space and provide a force in the superior and inferior directions. These forces press the implant fixation features of the prosthetic endplates into the vertebral endplates, thereby enhancing the resistance of the implant to movement.

Therefore, in accordance with the present invention, there is provided) an assembly for seating an implant in an intervertebral disc space, comprising:
  a) a first prosthetic endplate having an outer surface adapted for attachment to a first vertebrae and an inner surface having an articulation surface,
  b) a second prosthetic endplate having an outer surface adapted for attachment to a second vertebrae and an inner surface having an articulation surface,
  c) an endplate seating instrument comprising:
    i) a first longitudinal member having a distal end portion having an outer surface, an intermediate portion, and a proximal handle portion having an attachment point,
    ii) a second longitudinal member having a distal end portion having an outer surface, an intermediate portion, and a proximal handle portion having an attachment point,
    wherein the first and second longitudinal members are pivotally attached at a first pivot junction between the proximal handle and intermediate portions of each longitudinal member,
    wherein the outer surface of the distal end portion of the first longitudinal member contacts the inner surface of the first prosthetic endplate, and wherein the outer surface of the distal end portion of the second longitudinal member contacts the inner surface of the second prosthetic endplate.

DESCRIPTION OF THE FIGURES

FIGS. 1A and 1B disclose perspective views of the first embodiment of the present invention having four flanges adapted to bear against the anterior portion of the inner surface of the opposing prosthetic endplates, wherein the device is in its closed position.

FIGS. 1C and 1D disclose perspective views of the device of FIGS. 1A and 1B, wherein the device is in its open position.

FIGS. 2A and 2B disclose perspective views of the instrument of FIG. 1A acting upon an intervertebral motion disc.

FIGS. 3A and 3B disclose perspective views of the second embodiment of the present invention having extended flanges adapted to bear against the anterior and posterior portions of prosthetic endplates, wherein the device is in its closed position.

FIGS. 3C and 3D disclose perspective views of the device of FIG. 3A, wherein the device is in its open position.

FIGS. 4A and 4B disclose perspective views of the third embodiment of the present invention having flanges on only one longitudinal member of the instrument, wherein the device is in its closed position.

FIGS. 4C and 4D disclose perspective views of the device of FIG. 4A, wherein the device is in its open position.

DETAILED DESCRIPTION OF THE INVENTION

Figure 2C:
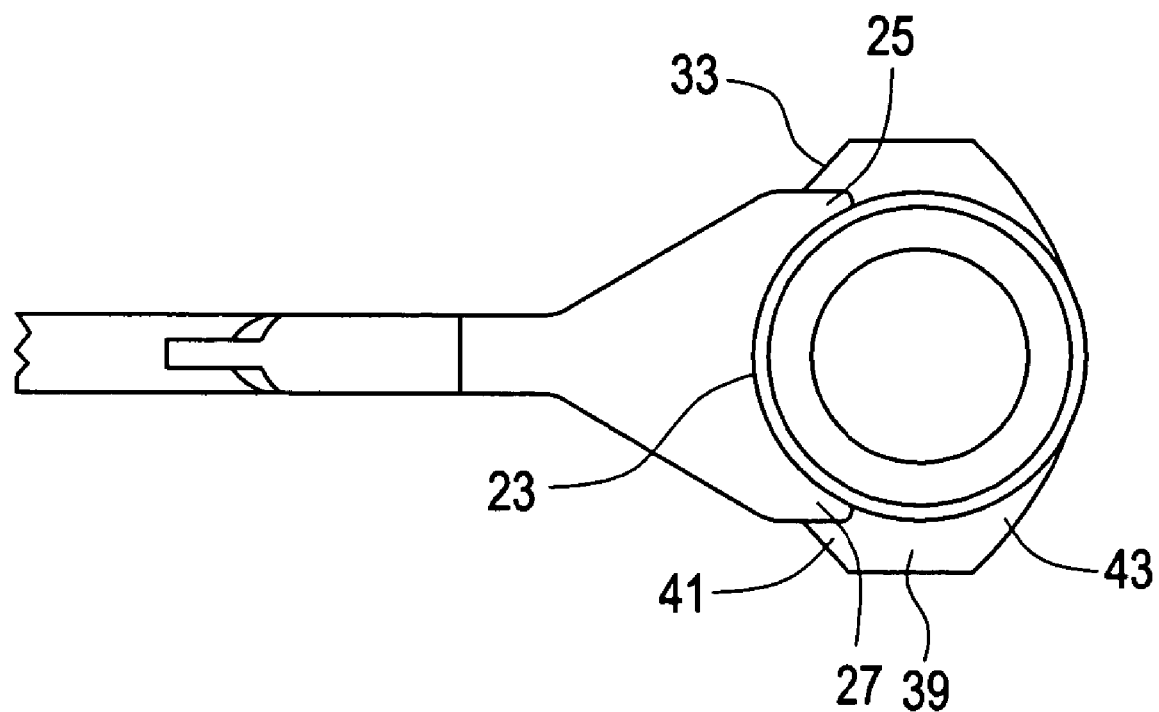
FIG. 2C discloses a bottom view of the flanges of the distal end portion of a first longitudinal member of the device of FIG. 2A contacting the inner surface of the first prosthetic endplate.
Figure 3E:
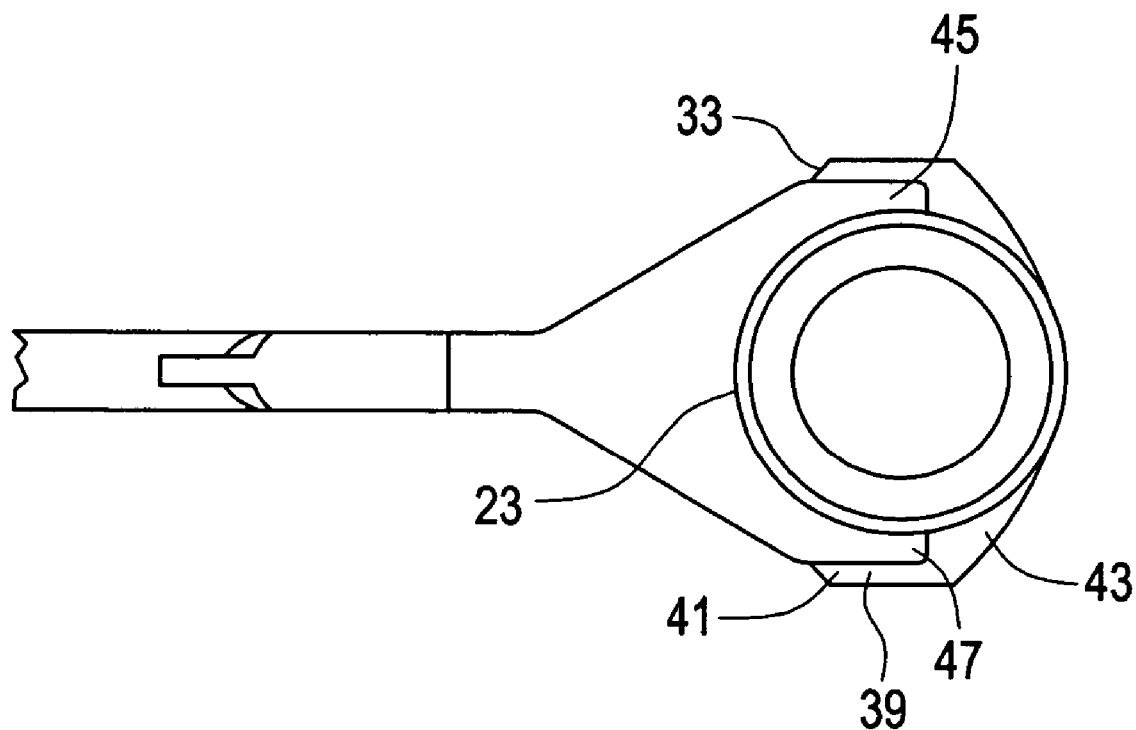
FIG. 3E discloses a bottom view of the extended flanges of the distal end portion of the first longitudinal member of the device of FIG. 3A contacting the anterior and posterior portions of the inner surface of the first prosthetic endplate.

Now referring to FIGS. 1A-1D, there is provided a first embodiment of the present invention, disclosing a seating instrument 1 for seating an endplate of an intervertberal motion disc having an anterior wall, an outer surface adapted for attachment to a vertebra and an inner surface, comprising:
  a) a first longitudinal member 3 having a distal end portion 5 having an outer surface 7, an intermediate portion 8, and a proximal handle portion 9,
  b) a second longitudinal member 11 having a distal end portion 15 having an outer surface 17, an intermediate portion 18, and a proximal handle portion 19, wherein the first and second longitudinal members are pivotally attached at a first pivot junction 21 within the intermediate portions of each longitudinal member, wherein the distal end portion of each longitudinal member comprises:
  i) a distal end wall 23 adapted to bear against the anterior end wall of the endplate of the motion disc,
  ii) a first flange 25 extending distally from the distal end wall and adapted to bear against the inner surface of the endplate of the motion disc, and
  iii) a second flange 27 extending distally from the distal end wall and adapted to bear against the inner surface of the endplate of the motion disc.

In the first embodiment, outer surfaces of the four flanges contact the anterior portions of the inner surface of each endplate and distract them in opposite directions to press the anteriorly—located fixation features of the outer surfaces of the prosthetic endplates into the bone.

Now referring to FIG. 2A, there is provided a perspective view of the instrument 1 of FIGS. 1A and 1B acting upon an intervertebral motion disc 31.

Now referring to FIG. 2B, there is provided a closeup perspective view of the distal end of FIG. 2A, showing greater detail of the intervertebral motion disc having an upper endplate 45, a lower endplate 47 and an articulating core 49 therebetween. Upper endplate 45 includes an anterior wall 33, an outer surface 35 comprising a plurality of teeth 37 adapted for attachment to a first vertebrae and an inner surface (not shown) having an articulation surface. Lower endplate 47 includes an outer surface (not shown) adapted for attachment to a first vertebrae and an inner surface 39 having an articulation surface (not shown), an anterior portion 41 and a posterior portion 43. The core resides between the articulaion surfaces of the upper and lower endplates.

Now referring to FIG. 2C, flanges 25, 27 of the endplate extend distally from the distal end wall 23 of the instrument and bear against the anterior portion 41 of the inner surface of the endplate of the motion disc. The distal end wall 23 of the instrument bears against the anterior wall 33 of the prosthetic endplate of the motion disc.

Now referring to FIGS. 3A-3E, there is provided a second embodiment of the present invention, wherein the flanges 45,47 of the instrument are distally extended. In this condition, each extended flange may extend distally in a manner sufficient to contact the posterior portion of the inner surface of each endplate. Now referring to FIG. 3E, extended flanges 45, 47 extend distally from the distal end wall 23 of the instrument and contact the anterior portion 41 and posterior portion 43 of the inner surface 39 of the endplate of the motion disc. The distal end wall 23 of the instrument bears against the anterior wall 33 of the endplate of the motion disc.

Because these flanges 45,47 reach further into the posterior recesses of the disc space, upon instrument actuation, they are able to press both anterior and posterior fixation features of the prosthetic endplate into the bony anatomy.

Now referring to FIGS. 4A-4D, there is provided a third embodiment of the present invention, disclosing a seating instrument 51 for seating an endplate of an intervertebral motion disc having an anterior wall, an outer surface adapted for attachment to a vertebra and an inner surface, comprising:
  a) a first longitudinal member 53 having a distal end portion 55 having an outer surface 57, an intermediate portion 58, and a proximal handle portion 59,
  b) a second longitudinal member 63 having a distal end portion 65 having an outer surface 67, an intermediate portion 68, and a proximal handle portion 69, wherein the first and second longitudinal members are pivotally attached at a first pivot junction 71 within the intermediate portions of each longitudinal member, wherein the distal end portion of the first longitudinal member comprises:
  i) a distal end wall 73 adapted to bear against the anterior end wall of the endplate of the motion disc,
  ii) a first flange 75 extending distally from the distal end wall and adapted to bear against the inner surface of the endplate of the motion disc,
  iii) a second flange 77 extending distally from the distal end wall and adapted to bear against the inner surface of the endplate of the motion disc, and wherein the distal end portion of the second longitudinal member comprises:
  i) a distal end wall 79 adapted to bear against the anterior end wall of the endplate of the motion disc.

In the third embodiment, the final seating instrument can be used to first press the fixation features of a first prosthetic endplate into the bony anatomy, and then press the fixation features of a second prosthetic endplate into the bony anatomy. In this embodiment, the distally extending flanges of the instrument press against the inner surface of one prosthetic endplate while the opposite distal end portion of the instrument rests upon the opposite vertebral body. Once the fixation features of one endplate have been seated, the instrument is flipped and the procedure is repeated to press the fixation features of the opposite prosthetic endplate into the bony anatomy.

In the fourth embodiments the final seating instrument comprises a single superior flange and a single inferior flange, and provides for unilateral seating of the opposed endplates.

Figure 5:
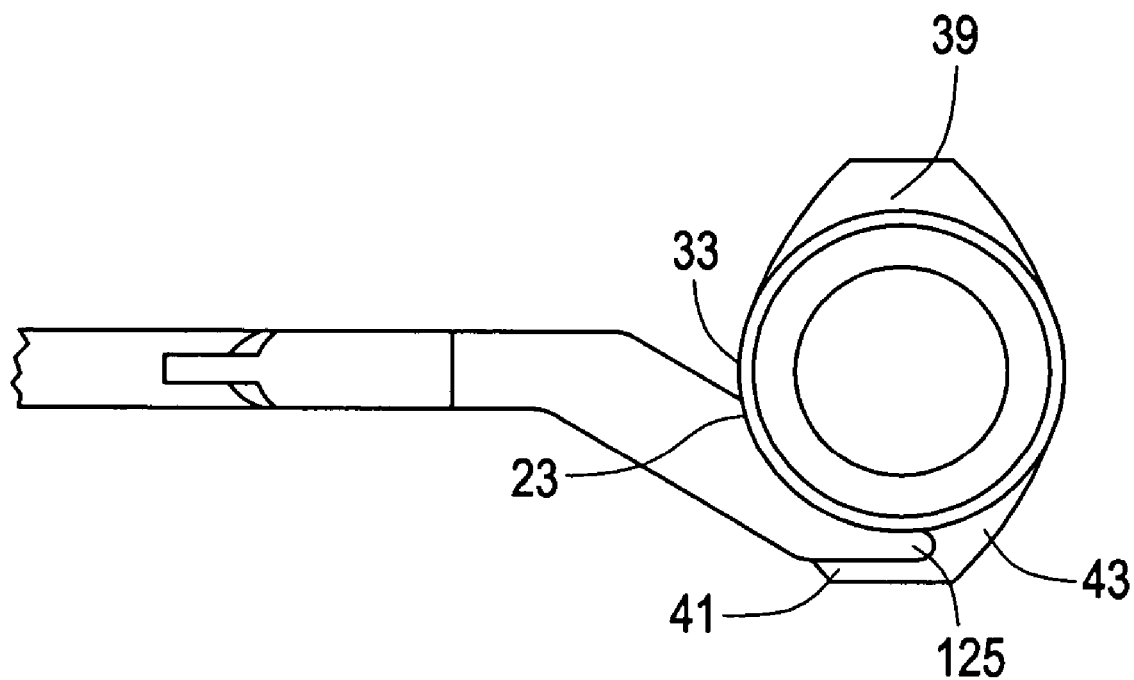
FIG. 5 discloses a bottom view of a fourth embodiment of the present invention having a single flange extending from the distal wall of the longitudinal member, wherein the flange contacts the inner surface of the first prosthetic endplate.

Now referring to FIG. 5A, the fourth embodiment includes a unilateral flange 125 extending distally from the distal end wall 23 of the instrument and bearing against the anterior portion 41 of the inner surface 39 of the endplate of the motion disc. The distal end wall 23 of the instrument bears against the anterior wall 33 of the endplate of the motion disc.

Therefore, in accordance with the present invention, there is provided a fourth embodiment of the present invention, disclosing a seating instrument for seating an endplate of an intervertebral motion disc having an anterior wall, an outer surface adapted for attachment to a vertebra and an inner surface, comprising:
  a) a first longitudinal member having a distal end portion having an outer surface, an intermediate portion, and a proximal handle portion having an attachment point,
  b) a second longitudinal member having a distal end portion having an outer surface, an intermediate portion, and a proximal handle portion having an attachment point, wherein the first and second longitudinal members are pivotally attached at a first pivot junction within the intermediate portions of each longitudinal member, wherein the distal end portion of each longitudinal member comprises:
  i) a distal end wall adapted to bear against the anterior end wall of the endplate of the motion disc, and
  ii) a first flange extending distally from the distal end wall and adapted to bear against the inner surface of the endplate of the motion disc.

In a fifth embodiment (not shown), the final seating instrument comprises nested flanges, wherein the nesting increases the strength of the instrument.

In some embodiments, the instrument of the present invention is integral. In other embodiments, the instrument of the present invention is provided with modular tips.

In some embodiments, the instrument of the present invention operates with a scissor-like, non-parallel pivoting arrangement. In other embodiments, the instrument of the present invention operates with a parallel action pivoting arrangement.

In some embodiments, as shown, the instrument may have a double action hinge. However, in other embodiments, the instrument may have a single action hinge.

Preferably, the first pivot junction is provided at a location sufficient to produce a mechanical advantage of at least 2:1, more preferably at least 5:1.

Typically, the components of the present invention can be made out of any material commonly used in medical instruments. If the device is designed to be reusable, then it is preferred that all the components be made of stainless steel. If the device is designed to be disposable, then it is preferred that some of the components be made of plastic. Preferably, at least one component is sterilized. More preferably, each component is sterilized.

Preferred articulating motion devices for use with the present invention are disclosed in U.S. Pat. Nos. 5,556,431 and 5,674,296, the specifications of which are incorporated by reference. These are three piece articulating motion discs.

In some embodiments, the general structure of the three piece articulating motion disc comprises:
- a) a first prosthetic vertebral endplate comprising:
  - i) an outer surface adapted to mate with a first vertebral body,
  - ii) an inner surface having a first articulation surface and a peripheral rim,
  - iii) a body portion connecting the inner and outer surfaces,
- b) a second prosthetic vertebral endplate comprising:
  - i) an outer surface adapted to mate with a second vertebral body, and
  - ii) an inner surface comprising a first articulation surface and a peripheral rim,
- c) a core member comprising:
  - i) a first articulation surface adapted for articulation with the first articulation surface of the first endplate, and
  - ii) a second articulation surface adapted for articulation with the first articulation surface of the second endplate, wherein the core member is oriented to produce a first articulation interface between the first articulation surface of the first endplate and the first articulation surface of the core member, and a second articulation interface between the first articulation surface of the second endplate and the second articulation surface of the core member.

In some embodiments, the general structure of the articulating motion disc is a two piece design and comprises:
- a) a first prosthetic vertebral endplate comprising:
  - i) an outer surface adapted to mate with a first vertebral body,
  - ii) an inner surface having a first articulation surface and a peripheral rim,
  - iii) a body portion connecting the inner and outer surfaces,
- b) a second prosthetic vertebral endplate comprising:
  - i) an outer surface adapted to mate with a second vertebral body, and
  - ii) an inner surface comprising a second articulation surface and a peripheral rim, wherein the first and second articulation surfaces are oriented produce an articulation interface.

Preferably, the articulation interfaces form partial spheres.

The instrument of the present invention can be adapted for use in the final seating of motion discs adapted for any of the lumbar, thoracic or cervical spine regions. In some embodiments wherein the motion disc is adapted for use in the lumbar region, the three-piece design having a core is selected. In some embodiments wherein the motion disc is adapted for use in the cervical region, the two-piece design is selected.

We claim:

1. An assembly for seating an implant in an intervertebral disc space, comprising:
   a) a first prosthetic endplate having an outer surface adapted for attachment to a first vertebrae and an inner surface having an articulation surface,
   b) a second prosthetic endplate having an outer surface adapted for attachment to a second vertebrae and an inner surface having an articulation surface,
   c) an endplate seating instrument comprising:
      i) a first longitudinal member having a distal end portion having an outermost surface, an intermediate portion, and a proximal handle portion having an attachment point,
      ii) a second longitudinal member having a distal end portion having an outermost surface, an intermediate portion, and a proximal handle portion having an attachment point,
      wherein the first and second longitudinal members are pivotally attached at a first pivot junction between the proximal handle and intermediate portions of each longitudinal member,
   wherein the outermost surface of the distal end portion of the first longitudinal member contacts the inner surface of the first prosthetic endplate,
   wherein the outermost surface of the distal end portion of the second longitudinal member contacts the inner surface of the second prosthetic endplate,
   wherein the distal end portion of each longitudinal member comprises:
      i) a distal end wall adapted to bear against the anterior end wall of the endplate of the implant, and
      ii) a first flange extending distally from the distal end wall and having an outer surface adapted to bear against the inner surface of the endplate of the implant,
      iii) a second flange extending distally from the distal end wall and adapted to bear against the inner surface of the endplate of the implant,
   wherein the inner surface of the endplate has a bearing surface, and the first and second flanges are adapted to straddle the bearing surface, and
   wherein the distal end wall has a midpoint, and the first and second flanges include a concave wall facing the midpoint.

2. The instrument of claim 1 wherein each endplate has a posterior portion, and each flange extends distal to contact the posterior portion of each endplate.

* * * * *